(12) United States Patent
Saferstein et al.

(10) Patent No.: US 7,645,874 B2
(45) Date of Patent: Jan. 12, 2010

(54) CELLULOSE OXIDATION BY NITROGEN DIOXIDE IN A PERFLUORINATED TERTIARY AMINE SOLVENT

(75) Inventors: Lowell Saferstein, West Orange, NJ (US); Gonzalo Serafica, Langhorne, PA (US)

(73) Assignee: Xylos Corporation, Langhorne, PA (US)

( * ) Notice: Subject to any disclaimer, the term of this patent is extended or adjusted under 35 U.S.C. 154(b) by 774 days.

(21) Appl. No.: 10/911,645

(22) Filed: Aug. 5, 2004

(65) Prior Publication Data

US 2007/0054880 A1 Mar. 8, 2007

(51) Int. Cl.
*C08B 1/00* (2006.01)
*C08B 15/06* (2006.01)
*C08B 37/00* (2006.01)
*C07H 1/00* (2006.01)
*C07H 3/00* (2006.01)
*C07H 5/04* (2006.01)
*C07H 5/06* (2006.01)

(52) U.S. Cl. .................. 536/55.3; 536/30; 536/56; 536/124

(58) Field of Classification Search ............... 8/115.51, 8/116.1, 181, 196; 536/30, 55.3, 56
See application file for complete search history.

(56) References Cited

U.S. PATENT DOCUMENTS

| | | | |
|---|---|---|---|
| 3,872,862 A | 3/1975 | Hume | |
| 5,180,398 A * | 1/1993 | Boardman et al. | 8/181 |
| 5,914,003 A * | 6/1999 | Kosowski et al. | 162/81 |
| 6,320,093 B1 | 11/2001 | Augustine et al. | |
| 2004/0040096 A1 | 3/2004 | Saferstein et al. | |

OTHER PUBLICATIONS http://www.epa.gov/hpv/pubs/summaries/perfluro/c13244rs.pdf (2001).*
Brown-Etris et al., "Evaluation of a Biosynthetic Material: A New Wound Dressing Concept," Abstract, 1 Sheet, presented as a poster around Apr. 1998.
"Some of These Companies Forecast Revenues of More Than $25 Million," May/Jun. 1999, 1 Sheet.
Redacted agreement, Exhibit A to Rule 132 Declaration of Russell Hoon.
Jun. 22, 1998 510(k) approval No. K974251 for X-Cell Wound Dressing (printed out from FDA web site).

* cited by examiner

*Primary Examiner*—Traviss C McIntosh, III
(74) *Attorney, Agent, or Firm*—Foley & Lardner LLP

(57) ABSTRACT

This invention relates to a process for preparing bioabsorbable oxidized cellulose comprising combining cellulose material, with nitrogen dioxide and a nonaqueous solvent chosen from the class of perfluorinated tertiary amines. This invention also relates to a method of oxidizing cellulose material comprising introducing a solvent into the vessel, circulating the solvent through the cellulose material, adding nitrogen dioxide to said vessel containing the solvent and cellulose in the required amounts, circulating the solution for 7 to 24 hours while controlling the reaction temperature, and isolating the oxidized material. Preferably, isolation of the oxidized product is followed by first washing the oxidized cellulose material with cold water, then washing the oxidized cellulose material with an aqueous alcohol solution several times, then washing the material with 100% alcohol several times, and finally drying the oxidized material.

29 Claims, No Drawings

CELLULOSE OXIDATION BY NITROGEN DIOXIDE IN A PERFLUORINATED TERTIARY AMINE SOLVENT

FIELD OF THE INVENTION

This invention relates to a process for oxidizing cellulose with a solution of nitrogen dioxide in one or more perfluorinated tertiary amine solvents.

BACKGROUND OF THE INVENTION

Oxidized cellulose has been known in the art for more than 50 years. Its ability to be absorbed by the body makes oxidized cellulose an attractive material for medical uses such as sutures, hemostats, wound coverings, and adhesion prevention devices. Several oxidizing agents can be used to oxidize cellulose including metaperiodate, hypochlorite and dichromate. However, the only suitable method for preparing material that is bioabsorbable and maintains the appropriate physical properties is by oxidation with nitrogen dioxide.

Early work on the oxidation of cellulose to produce bioabsorbable cellulose was conducted by W. O. Kenyon and others at Tennessee Eastman (for example see U.S. Pat. No. 2,423,707 issued Jul. 8, 1947 to Kenyon et al., and R. H. Hasek et al. "Oxidation of Cellulose," Ind. & Eng. Chem., Vol. 41, p. 2 (1949)). In these pioneering oxidation processes, they found that cellulose was oxidized by using either gaseous nitrogen dioxide or a solution of nitrogen dioxide in a chlorinated hydrocarbon solvent such as carbon tetrachloride.

Carbon tetrachloride was initially investigated by Kenyon as an inert solvent for oxidation of cellulose with nitrogen dioxide. Other solvents were also tested by scientists in the field. W. H. Ashton et al. in U.S. Pat. No. 3,364,200 discloses a process for preparing oxidized cellulose in nonaqueous solvents such as Freon 113 ($CCl_2FCClF_2$) and Freon 11 ($CCl_3F$). The use of chlorinated hydrocarbons and chlorinated fluorocarbons (CFCs) were disclosed by B. G. Yasnitsky in U.S. Pat. No. 4,347,057.

The success of these solvents turned on their failure to interact with the oxidizing agent. It is critical for the oxidation process that the solvent not react with the oxidizing agent (nitrogen dioxide) otherwise the solvent will be destroyed and the oxidizing agent will be spent in reacting with the solvent rather than with the cellulose material. Organic solvents containing a carbon hydrogen bond are all susceptible to reaction with nitrogen dioxide. This need for the solvent to be inert with respect to nitrogen dioxide severely limits the number of organic solvents available for use in this reaction.

Further, there were problems associated with the inert organic solvents used in this process. Chlorinated hydrocarbons and chlorinated fluorocarbons (Freon type solvents) were found to pose environmental problems related to the depletion of the ozone layer at high altitudes. It is believed that the carbon chlorine bond (C—Cl) in these molecules is ruptured in the stratosphere to produce chlorine radicals which go on to destroy ozone. Carbon fluorine bonds (C—F) are stronger than carbon chlorine bonds and are not ruptured by radiation in the stratosphere, thus fluorocarbons do not deplete the ozone layer.

In an effort to oxidize cellulose and minimize the problems associated with the organic solvents, U.S. Pat. No. 5,180,398 by Boardman et al. teaches a process for oxidizing cellulose with a solution of nitrogen dioxide in a perfluorohydrocarbon solvent. The perfluorohydrocarbon solvents that are used are inert to the nitrogen dioxide and supposedly do not destroy the ozone layer of the earth. U.S. Pat. No. 5,914,003 by Kosowski et al. also discloses a process for effectively oxidizing cellulose with nitrogen dioxide but uses a solution of a hydrofluoroether solvent. However, the hydrofluoroether solvents cited by the author are not fully fluorinated compounds but, in fact, contain carbon hydrogen bonds and thus are not totally inert to the oxidizing agent.

SUMMARY OF THE INVENTION

This invention relates to a process for preparing bioabsorbable oxidized cellulose comprising combining cellulose material, with nitrogen dioxide and a nonaqueous solvent chosen from the class of perfluorinated tertiary amines. This invention also relates to a method of oxidizing cellulose material comprising introducing a solvent into the vessel, circulating the solvent through the cellulose material, adding nitrogen dioxide to said vessel containing the solvent and cellulose in the required amounts, circulating the solution for 7 to 24 hours while controlling the reaction temperature, and isolating the oxidized material. Preferably, isolation of the oxidized product is followed by first washing the oxidized cellulose material with cold water, then washing the oxidized cellulose material with an aqueous alcohol solution several times, then washing the material with 100% alcohol several times, and finally drying the oxidized material.

The present inventors have discovered that perfluorinated tertiary amines are effective solvents for nitrogen dioxide in the oxidation of cellulose to form bioabsorbable oxidized cellulose. The perfluorinated tertiary amines are clear, colorless, odorless, non flammable liquids. They are non-irritating to the eyes and skin and are practically non-toxic orally. They contain no carbon hydrogen bonds. They also demonstrate very low acute and sub-chronic inhalation toxicity. The perfluorinated tertiary amines have zero ozone depletion potential and are not classified as volatile organic compounds.

The invention provides methods for using perfluoro-tertiary amines with nitrogen dioxide to effectively oxidize cellulose to bioabsorbable oxidized cellulose for medicinal uses such as sutures, hemostats, wound coverings, and adhesion prevention devices. The class of perfluorinated tertiary amines have the formula $N(C_xF_{2x+1})_3$ where x is a whole number from 1-10. Especially preferred is perfluorotripropyl amine where x=3 available from 3M Corporation as FC-3283. The process avoids the use of environmentally undesirable solvents such as chlorinated hydrocarbon or chlorofluorohydrocarbons (CFC's) or perfluoroethers that contain carbon hydrogen bonds The use of amines as a solvent for oxidation has not been recognized previously because they were believed to neutralize nitrogen dioxide. In fact, the prior art teaches away from using amine solvents in an oxidizing reaction. In an article that appeared in the Russian literature (M. M. Pavlyuchenko et al. "Influence of the Nature of Organic Solvents on the Interaction of Cellulose with Nitrogen Dioxide," Zh. Prikl. Khim., Vol. 48, No. 8, (1975)), Pavlyuchenko states that polar solvents such as ethers and amines are not effective for oxidation. However, the present invention has discovered that although aliphatic tertiary amines will neutralize nitrogen dioxide and render it ineffective for oxidation, perfluorinated tertiary amines do not neutralize nitrogen dioxide. Perfluorinated tertiary amines are unusual compounds. They are not strong bases as are aliphatic tertiary amines. Rather, perfluorinated tertiary amines are neutral and do not interact with nitrogen dioxide and thus, are effective solvents for the oxidation of cellulose with nitrogen dioxide.

As discovered in the present invention, the neutral character of perfluorinated tertiary amines comes about from the strong electron withdrawing properties of the fluorine atom. The free pair of electrons on the nitrogen atom of the perfluorinated tertiary amines is surrounded in an environment of fluorine atoms which strongly pull the electrons from the nitrogen atom towards the fluorine atoms. Consequently, the Lewis Base character of the amine nitrogen in perfluorinated tertiary amines is weakened to such an extent that this class of compounds is in fact neutral exhibiting no amine, electron donor or base like character.

Several advantages of using perfluorinated tertiary amines as solvents for nitrogen dioxide in the oxidation of cellulose have been identified by this invention. For example, their low vapor pressure compared to perfluorinated hydrocarbons reduces their volatility and loss, making recovery economical. Further, perfluorinated hydrocarbon compounds generally are poor solvents for most materials except other perfluorinated compounds. However, the perfluorinated tertiary amine solvents are good solvents for nitrogen dioxide and consequently during oxidation reactions the nitrogen dioxide is adequately soluble in the solvent and the oxidation proceeds in a gentile manner which minimizes loss of physical properties of the cellulose. Good solvents for nitrogen dioxide tend to bring about mild oxidation of cellulose resulting in a soft, pliable oxidized fabric whereas those solvents that exhibit a low solubility for nitrogen dioxide tend to produce harsh, stiff oxidized fabrics.

This invention identifies cellulose material suitable for oxidation by this process. The cellulose material can be selected from any cellulose form including powders, sponges, knitted, woven and non-woven fabrics made of cotton, rayon or lyocell fibers, and the generic name of cellulose textile fibers spun from N-methylmorpholine-N-oxide solution. Also included in the type of cellulose that this oxidation process can accommodate are cellulose films, cellulose paper, cotton or rayon balls, fibers of cotton or rayon or lyocell, or a pellicle of cellulose produced by *Acetobacter xylinum*.

The oxidation process is accomplished by first introducing the cellulose material into a reaction vessel. Solvent is added to the vessel and circulated through the cellulose. Nitrogen dioxide is then added in the required amounts and the solution is circulated for the appropriate period of time generally from 7 to 24 hours. The temperature of the reaction is controlled and can be adjusted from −20° C. to 60° C. preferably between 25° C. and 50° C. The temperature can be held constant during the oxidation process or adjusted to higher or lower values as desired. The reaction can be run in a pressure vessel or a vessel vented to the atmosphere.

Achieving the desired degree of oxidation involves varying the nitrogen dioxide concentration in the solvent and the temperature and duration of the reaction. Low solution concentrations of nitrogen dioxide lead to long reaction times. On the other hand, high concentrations of nitrogen dioxide can cause physical damage to the cellulose leading to stiff or degraded material. Generally, a concentration of nitrogen dioxide of 5-15% is preferred. The ratio of nitrogen dioxide to cellulose can be 0.5 to 5 preferably 0.8 to 3.

Isolation of the oxidized material is achieved by removing the solution from the vessel and adding it to an aqueous solution of dilute sodium hydroxide which neutralizes the unreacted nitrogen dioxide. The perfluorinated tertiary amine will separate from the water and settle to the bottom of the vessel where it can be recovered to be used again. The oxidized cellulose material is washed with cold water to remove any residual nitrogen dioxide and then washed with an aqueous alcohol solution to remove additional acid and perfluorinated solvent. After several aqueous alcohol washes the oxidized material is washed in 100% alcohol such as isopropyl alcohol, ethyl alcohol or methyl alcohol several times to remove water and then dried.

SUMMARY OF THE PREFERRED EMBODIMENTS

Unless otherwise specified, the words "a" or "an" as used herein mean "one or more".

The present invention further includes the following numbered embodiments:

1. A process for preparing bioabsorbable oxidized cellulose comprising combining cellulose material, with nitrogen dioxide and a nonaqueous solvent chosen from the class of perfluorinated tertiary amines.

2. The process according to embodiment 1 wherein the formula for the class of perfluorinated tertiary amines is $N(C_xF_{2X+1})_3$ wherein X is a whole number from 1-10.

3. The process according to embodiment 2 where the formula for the class of perfluorinated tertiary amines is $N(C_xF_{2X+1})_3$ wherein X is 3.

4. The process according to embodiment 1 where the cellulose material can be selected from the group consisting of powders, sponges, knitted, woven, and non-woven fabrics.

5. The process according to embodiment 4 where the non-woven fabric is selected from the group consisting of cotton, rayon, or lyocell fibers.

6. The process according to embodiment 1 where the cellulose material can be selected from the group consisting of cellulose films, cellulose paper, cotton, or rayon balls, fibers of cotton or rayon or lyocell, or a pellicle of cellulose produced by *Acetobacter xylinum*.

7. The process according to embodiment 1 wherein the ratio of nitrogen dioxide to cellulose is about 0.5 to 5.

8. The process according to embodiment 7 wherein the determined amount of nitrogen dioxide to cellulose ratio is about 0.8 to 3.

9. The process according to embodiment 1 wherein the nitrogen dioxide has a concentration of 5-15%.

10. The process of embodiment 1, wherein the cellulose of each embodiment is preferably microbial cellulose, and more preferably it is microbial cellulose from *Acetobacter xylinum*.

11. The process of oxidizing cellulose material comprising introducing an appropriate amount of non-aqueous solvent from the class of perfluorinated tertiary amines into a vessel containing an appropriate amount of cellulose material, circulating the solvent through the cellulose material, adding an appropriate amount of nitrogen dioxide to said vessel containing the solvent and cellulose material, circulating the solution for 7 to 24 hours while controlling the reaction temperature, isolating the oxidized material.

12. The process of embodiment 11, wherein the remaining solution from the vessel is preferably added to an aqueous solution of dilute sodium hydroxide.

13. The process of embodiment 11, wherein following isolation of the oxidized cellulose, it is preferably further treated by first washing the oxidized cellulose material with cold water, then washing the oxidized cellulose material with an aqueous alcohol solution several times, then washing the solution with 100% alcohol several times, and finally drying the oxidized material in the air, in an oven, or using supercritical fluid.

14. The method according to embodiment 10 wherein the cellulose material achieves its desired degree of oxidation by varying the nitrogen dioxide concentration in the solvent and the temperature and the duration of the reaction.

15. The method according to embodiment 10 where the reaction temperature is from −20° C. to 60° C. or more preferably 25° C. to 50° C. and can be held constant or vary.

16. The method of embodiment 10 wherein the reaction duration time is allowed to vary or is prolonged by using low solution concentrations of nitrogen dioxide.

17. The method according to embodiment 10 where the vessel is a pressure vessel or a vented vessel.

18. The method according to embodiment 10 where the appropriate amounts to combine of nitrogen dioxide and cellulose is in a 0.5 to 5 ratio.

19. The method according to embodiment 10 where the appropriate amounts to combine of nitrogen dioxide to cellulose is in a 0.8 to 3 ratio.

20. The method of embodiment 10 wherein the concentration of nitrogen dioxide in the solvent is varied.

21. The method according to embodiment 10 where the alcohol is selected from the group consisting of isopropyl alcohol, ethyl alcohol, or methyl alcohol.

The invention is further illustrated by, though in no way limited to, the following examples.

EXAMPLE 1

Oxidation of Cotton Pellets in Perfluorotributyl Amine Solvent

Six grams of cotton pellets were placed into a 500 ml resin kettle. In an ice bath 175 grams of perfluorotributyl amine (FC-40, boiling point 155° C. from 3M Corporation) were chilled. Fifteen grams of nitrogen dioxide were added to this chilled solvent before the chilled solution of nitrogen dioxide in the perfluorinated tributyl amine solvent was added to the resin kettle. The resin kettle was placed in a water bath and the temperature is brought up to 30° C. A condenser vented to a caustic trap was used in order to neutralize the nitrogen dioxide that escaped. The reaction was slowly stirred by an over head stirrer attached to the resin kettle for 20 hours, at which time the water bath was removed and the solution of nitrogen dioxide in the perfluorinated tributyl amine solvent was removed by pouring it into a solution of dilute sodium hydroxide. The cotton pellets are removed from the resin kettle and placed in 100 ml of chilled distilled water for 5 minutes, followed by a second wash in cold distilled water.

The cotton pellets were then placed in 100 ml of a 50:50 water: isopropyl alcohol solution and stirred gently for 10 minutes. The cotton pellets were filtered away from the 50:50 water: isopropyl wash solution and placed in another 100 ml of fresh 50:50 isopropyl alcohol: water wash and stirred for 10 minutes. A total of four 50:50 isopropyl alcohol: water washes were carried out. The cotton pellets were then placed in 100 ml of 100% isopropyl alcohol and stirred for 10 minutes to remove water. After repeating this 100% isopropyl alcohol wash a total of three times, the pellets were then removed and air dried.

One gram of the dry pellets was further dried at 70° C. for one hour in an oven. The dried pellet was weighed and then dissolved in 10 ml of 0.50N sodium hydroxide solution and diluted with 100 ml of distilled water. A clear slightly yellow solution resulted. The solution was titrated with standard 0.1N hydrochloric acid to a phenolphthalein end point. A blank was also run using only the sodium hydroxide solution. The carboxyl content of the cotton pellets calculated from back titration of the sodium hydroxide was 16.5%.

EXAMPLE 2

Oxidation of Non-Woven Rayon Fabric in Perfluorotriamyl Amine Solvent

The invention is further illustrated by, though in no way limited to, the following examples.

Into a 500 ml resin kettle were placed 5 grams of a non-woven rayon fabric. Into 150 grams of chilled perfluorotriamyl amine, (FC-70 boiling point 215° C. from 3M Corp.) were added 10 grams of nitrogen dioxide. This chilled solution was added to the resin kettle. A condenser attached to the resin kettle vented into a caustic solution in order to neutralize any nitrogen dioxide gas that escaped from the resin kettle. A water bath under the resin kettle was brought to 30° C. and held there for 18 hours. Bubbles of gas could be observed rising from the perfluorotriamyl amine solution during the course of the reaction. At the end of the 18 hours, the nitrogen dioxide solution was carefully poured into several liters of dilute sodium hydroxide to neutralize the unreacted nitrogen dioxide and to recover the perfluorotriamyl amine solvent. The oxidized rayon fabric was removed from the resin kettle and washed in 200 ml of chilled distilled water for 10 minutes. The cloth was then washed four times in 150 ml of a 50:50 isopropyl alcohol: water wash. This was followed by three washes in 150 ml of 100% isopropyl alcohol. The oxidized cloth was then air dried.

One gram of the dry cloth was further dried at 70° C. for one hour in an oven. The dried cloth was weighed and then dissolved in 10 ml of 0.50N sodium hydroxide solution and diluted with 100 ml of distilled water. A clear slightly yellow solution resulted. The solution was titrated with standard 0.1N hydrochloric acid to a phenolphthalein end point. A blank was also run using only the sodium hydroxide solution. The carboxyl content of the rayon cloth calculated from back titration of the sodium hydroxide was 14.5%.

EXAMPLE 3

Oxidation in Perfluorotripropyl Amine Solvent of Cellulose Produced by *Acetobacter xylinum*

Into a 500 ml resin kettle equipped with a magnetic stirring bar, 6 dry cellulose pellicles from *Acetobacter Xylinum* that have been cut into 7×7 cm. squares were placed. The dry pellicles weighed a total of 3.0 grams. 19 grams of nitrogen dioxide were dissolved into 140 grams of perfluorotripropyl amine solvent (FC-3283 from 3M Corp. boiling point of 128° C.) The nitrogen dioxide solution was added to the resin kettle. A condenser attached to the resin kettle was vented to a caustic bath to neutralize the gas that escaped from the kettle. The resin kettle was heated with a water bath that is held at 30° C. The reaction is run for 22.5 hours.

At the end of this time period, the solution was carefully poured into one liter of dilute sodium hydroxide solution to neutralize the excess nitrogen dioxide and to recover the perfluorotripropyl amine solvent. The pellicles were placed in 250 ml of cold distilled water for 10 minutes then placed in a second cold water wash for 10 minutes. The pellicles were removed from the cold water wash and allowed to soak for 10 minutes in 200 ml of a 50:50 isopropyl alcohol:water solution. This wash was repeated for a total of three times with fresh solvent for each wash. Finally the oxidized pellicles were placed in 200 ml of 100% isopropyl alcohol for 10 minutes to remove water. This 100% isopropyl alcohol wash was repeated a total of 3 times. The pellicles were then allowed to air dry.

One gram of the dry oxidized cellulose pellicle was further dried at 70° C. for one hour in an oven. The dried pellicle was weighed and then dissolved in 10 ml of 0.50N sodium hydroxide solution and diluted with 100 ml of distilled water. A clear slightly yellow solution resulted. The solution was titrated with standard 0.1N hydrochloric acid to a phenolphthalein end point. A blank was also run using only the sodium hydroxide solution. The carboxyl content of the oxidized pellicle calculated from back titration of the sodium hydroxide was 14.8%.

EXAMPLE 4

Comparison of Oxidized Cellulose Produced Using Two Different Solvents

The objective of these experiments was to investigate the differences in the chemical and physical properties of pellicles oxidized in a perfluorinated hydrocarbon solvent versus those pellicles oxidized in a perfluorinated tertiary amine solvent.

In addition, this experiment was also designed to evaluate the oxidation of super absorbent pellicles versus previous oxidations on solvent dried pellicles, and the use of supercritical $CO_2$ to dry the corresponding oxidized pellicles.

Super Absorbent Pellicles were cut into 3.7 cm disks. Solvents for the oxidation reactions were perfluoro-tripropylamine, FC-3283 from 3M Corporation with a boiling point of 128° C. and perfluoro hexane, PF-5060 also from 3M with a boiling point of 56° C.

Twenty-two disks were placed in one 100 ml resin kettle and another 22 disks were placed in a second 100 ml resin kettle each with a magnetic stir bar on the bottom. The total weight of the disks in the first resin kettle was 1.36 g. The weight of the 22 pellicles in the second resin kettle was 1.27 g.

Each resin kettle has an outlet connected with rubber tubing to a caustic trap to catch the vapors of nitrogen dioxide. Reactions were run at room temperature (~80° F.) for 23 hours. The solvents were pre-chilled in an ice bath. To 136 g of the perfluorinated tertiary amine solvent (FC-3283) were added to 16 g of liquid nitrogen dioxide. This solution was quickly poured into resin kettle number one and the magnetic stirrer was started. The pellicles floated up in the solvent necessitating a glass stopper to be placed on the top-most pellicle to gently push the 22 pellicles under the liquid.

Bubbles began to rise in the resin kettle as the solution warmed to room temperature.
Ratio of wt. FC-3283:pellicles=136/1.36=100:1
Ratio of $N_2O_4$:wt. pellicles=16/1.36=11.7:1
Conc. of $N_2O_4$=16/136×100=11.7%

To 127 grams of the pre-chilled PF-5060 solvent was added 16 grams of nitrogen dioxide liquid. This solution was quickly added to the second resin kettle and a glass stopper was placed on the top-most pellicle to submerge the column of disks under the solution. The magnetic stirrer was started and the solution was allowed to warm to room temperature. Bubbles were observed rising in the resin kettle indicating that oxidation had begun.
Ratio of wt. PF-5060:pellicles=127:1.27=100:1
Ratio of $N_2O_4$:wt. pellicles=16:1.27=12.6:1
Conc. of $N_2O_4$=16/127×100=12.6%

The oxidation conditions in both reactions were very similar so that any differences in the chemical or physical properties of the pellicles could be attributed to the solvents and not the conditions of oxidation.

Supercritical $CO_2$ was used to dry the pellicles and maintain their porosity.

Evaluation of the Samples Prepared with the Two Solvents

Carboxylic Content Measurement

Both reactions were stopped at 23 hours. Pellicles were removed from the resin kettles and placed in beakers with 100 ml of methyl alcohol. The pellicles were allowed to soak in the alcohol for 20 minutes at which time the alcohol was decanted off and replaced with fresh alcohol. This procedure was repeated for a total of three alcohol washes for each of the two batches of pellicles. Samples were soaked in methanol and placed into a supercritical fluid extractor.

The pellicles were selected at random from each batch and dried with light heat to constant weight. Pellicles were placed in 10 ml of 0.5 N sodium hydroxide and titrated with 0.1 N HCl.

The results of the titration shows that the level of oxidation using the perfluoroamine solvent were slightly higher (15.8%) as compared to the perfluorocarbon (15.0%). Thus it can be stated that the perfluoroamine solvent, with a slightly lower concentration in the oxidizing solution of 11.7%, was able to oxidize the samples slightly better than the perfluorocarbon solvent (12.6%).

Physical Evaluation

Pellicles from the two sample groups were randomly selected and their tensile strength was measured using a Testing Machine SSTM-2KN. Four samples from each group were tested and their average tensile strength (N) and elongation (%) is as follows;

Pefluoroamine solvent samples had an average tensile strength of 2.56 N and elongation of 5.72%. On the other hand, perfluorocarbon solvent samples had an average tensile strength of 5.85 N and elongation of 6.14%.

Based on these findings, it shows that the perfluoroamine samples had a lower tensile strength than the perfluorocarbon samples which can be attributed to its slightly higher degree of oxidation at the same operating conditions.

Degradation Properties

Pellicles from the two sample groups were randomly selected and their degradation over time in buffer solution was measured. Each of the samples was soaked in 20 ml of phosphate buffer solution pH 7.4 and aliquot portions of the supernatant were tested for their absorption at a wavelength of 240 nm using a UV-Vis spectrophotometer. Physical observations of the samples were also recorded at each time point. The absorbance at different time points in shown below.

| Sample | 6 Hour | 24 Hour | 48 Hour | 72 Hour |
| --- | --- | --- | --- | --- |
| PFA Buffer A | 0.046 | 0.376 | 0.6 | 1.16 |
| PFA Buffer B | −0.05 | 0.352 | 0.529 | 0.946 |
| PFC Buffer A | −0.91 | 0.18 | 0.268 | 0.399 |
| PFC Buffer B | −0.074 | 0.216 | 0.264 | 0.461 |

As can be observed, the absorbance which is an indirect measure of the degradation rate of the samples show a faster degradation of the perfluoroamine samples (PFA) as compared to the perfluorocarbon samples. Physical observation of the samples also showed slightly faster dissolution of the PFA samples in buffer solution after 72 hours as compared to the PFC samples. These results are probably due to the higher oxidation achieved using the PFA solvent than the PFC samples. Thus, the results of all these evaluations support the conclusion that the perfluoroamine solvent is slight better solvent for nitrogen tetroxide than perfluorocarbon solvents and can effect a slightly higher degree of oxidation resulting to faster degradation.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All publications and references cited herein are incorporated by reference in their entireties to the same extend as if each was individually incorporated by reference.

What is claimed is:

1. A method of making bioabsorbable oxidized cellulose comprising combining cellulose obtained from *Acetobacter xylinum*, nitrogen dioxide and a non-aqueous solvent selected from the group consisting of perfluorinated tertiary amines, wherein the oxidized cellulose has lower tensile strength and greater elongation than an oxidized cellulose produced with use of a perfluorinated hydrocarbon solvent under equivalent operating conditions.

2. A method of making the bioabsorbable oxidized cellulose of claim 1 comprising:
    a. introducing a cellulose material into a reaction vessel;
    b. introducing a solvent into the reaction vessel of step (a);
    c. circulating the solvent through the cellulose material;
    d. adding the required amount of nitrogen dioxide to the reaction vessel containing the solvent and the cellulose material to make a solution;
    e. circulating the solution for a period of time while controlling the reaction temperature; and
    f. isolating the cellulose material after the desired degree of oxidation has been achieved.

3. The method of claim 2 wherein the solvent is selected from a group of perfluorinated tertiary amines with the formula $N(C_xF_{2x+1})_3$, wherein x is a whole number from 1 to 10.

4. The method of claim 3 wherein x is 3.

5. The method of claim 2 wherein the desired degree of oxidation is achieved by varying a factor selected from the group consisting of nitrogen concentration, reaction temperature, reaction duration or a combination of these factors.

6. The method of claim 2 wherein the appropriate amount of nitrogen dioxide ranges from 5% to 15%.

7. The method of claim 2 wherein the appropriate amount of nitrogen dioxide is a ratio of nitrogen dioxide to cellulose that ranges from 0.5 to 5.

8. The method of claim 7 wherein the ratio ranges from 0.8 to 3.

9. The method of claim 2 wherein the amount of nitrogen dioxide in the solution is varied throughout the duration of the reaction.

10. The method of claim 2 wherein the temperature is between −20° C. and 60° C.

11. The method of claim 2 wherein the temperature is between 25° C. and 50° C.

12. The method of claim 2 wherein the temperature is constant throughout the oxidation process.

13. The method of claim 2 wherein the temperature is adjusted during the oxidation process.

14. The method of claim 2 wherein the solution is circulated for 6 hours to 24 hours.

15. The method of claim 2 wherein the solution is circulated for 8 hours to 12 hours.

16. The method of claim 2 wherein the degree of oxidation is achieved by varying the duration of the reaction.

17. The method of claim 2 wherein the vessel is a pressure vessel.

18. The method of claim 2 wherein the vessel is a vessel vented to the atmosphere.

19. The method of claim 2 wherein the oxidized material is isolated comprising:
    a. removing the oxidized cellulose material;
    b. placing the material in an aqueous solution;
    c. removing the material from the aqueous solution;
    d. performing a first washing of the oxidized cellulose material;
    e. performing a second washing of the oxidized cellulose material;
    f. performing a third washing of the oxidized cellulose material; and
    g. drying the oxidized cellulose material.

20. The method of claim 19 wherein the aqueous solution is dilute sodium hydroxide comprising a concentration of less that 0.5N NaOH.

21. The method of claim 19 wherein the first washing is performed using water that is below 20° C.

22. The method of claim 19 wherein the second washing is performed using an aqueous alcohol solution comprising a percentage of alcohol equal to or greater than 50%.

23. The method of claim 22 wherein the alcohol is selected from the group consisting of isopropyl, ethyl, or methyl alcohol.

24. The method of claim 22 wherein the second washing is performed at least two times or at least until there is no visible sign of nitrogen tetroxide in the sample.

25. The method of claim 19 wherein the third washing is performed with 100% alcohol.

26. The method of claim 25 wherein the alcohol is selected from the group consisting of isopropyl, ethyl, or methyl alcohol.

27. The method of claim 25 wherein the third washing is performed until the residual water in the sample is less than 1%.

28. The method of claim 19 wherein the oxidized cellulose material is dried by a method selected from the group consisting of air-dried, oven dried, or supercritical fluid drying.

29. The method of claim 28 wherein the supercritical fluid is $CO_2$.

* * * * *

UNITED STATES PATENT AND TRADEMARK OFFICE
CERTIFICATE OF CORRECTION

PATENT NO. : 7,645,874 B2
APPLICATION NO. : 10/911645
DATED : January 12, 2010
INVENTOR(S) : Saferstein et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1421 days.

Signed and Sealed this

Sixteenth Day of November, 2010

David J. Kappos
*Director of the United States Patent and Trademark Office*